(12) United States Patent
Aichinger et al.

(10) Patent No.: US 6,924,143 B2
(45) Date of Patent: Aug. 2, 2005

(54) METHOD FOR INCREASING THE GROWTH RATE OF CELLS IN STATIC LIQUID MEDIA

(75) Inventors: Christian Aichinger, Köln (DE); Peter Schreier, Köln (DE); Dana Schöneberg, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/252,500

(22) Filed: Sep. 23, 2002

(65) Prior Publication Data

US 2003/0092165 A1 May 15, 2003

(30) Foreign Application Priority Data

Oct. 11, 2001 (DE) ........................................ 101 50 311

(51) Int. Cl.⁷ ................................................. C12N 5/00
(52) U.S. Cl. .................... 435/383; 435/254.1; 435/325; 435/348; 435/410
(58) Field of Search .............................. 435/254.1, 325, 435/348, 383, 410, 243, 375, 404

(56) References Cited

U.S. PATENT DOCUMENTS 4,450,233 A    5/1984   Mimura et al. ............. 435/178

FOREIGN PATENT DOCUMENTS

| EP | 0 164 888 | 12/1985 |
| WO | 01/73099 | 10/2001 |

OTHER PUBLICATIONS

Indian J. Microbiol. 29, Jun. 1989, pp. 83–117, S.F. D'Souza, "Immobiliaed Cells: Techniques and Applications".

Biotechnology Advances, 18, (month unavailable) 2000, pp. 549–579, "Xanthan gum: production, recovery, and properties" by F. Garcia–Ochoa, V. E. Santos, J. A. Casas, and E. Gómez.

Handbook of Genetics, vol. 1, (month unavailable) 1974, pp. 575–595, "Ustilago maydis" by Robin Holliday.

Weed Technology, (month unavailable) 1997, vol. 11, pp. 212–220, "An Evaluation of Hydrophilic Polymers for Formulating the Bioherbicide Agents *Alternaria cassiae* and *A. eichhornia*" by Y. M. Shabana, R. Charudattan, J. T. Devalerio, and M. A. Elwakii.

Molecular and Cellular Biology, Sep. 1988, pp. 3703–3709, "Isolation and Characterization of an Autonomously Replicating Sequence from *Ustilago maydis*" bu T. Tsukuda, S. Carleton, S. Fotheringham and W. K. Holloman.

Mol Gen Genet, (month unavailable) 1996, 252, pp. 503–509, "Green fluorescent protein (GFP) as a new vital marker in the phytopathogenic fungus *Ustilago maydis*" by T. Spellig, A. Bottin and R. Kahmann.

Database WPI 'Online!, Derwent Publications Ltd., London, GB; Ungarisches Patent HU30776, (Mar. 28, 1984), "Binder for viscous culture medium– comprises microcrystalline cellulose and agar–agar." retrieved from WPI, Database accession No. 1984–122671, XP002224284, Seite 1, Absatz 1.

*Primary Examiner*—David M. Naff
*Assistant Examiner*—Deborah K. Ware
(74) *Attorney, Agent, or Firm*—Richard E. L. Henderson; Raymond J. Harmuth (57) ABSTRACT

The present invention relates to a method for increasing the growth rate of cells in static liquid media by using gelatinising agents and to a method for increasing the expression of genes in these cells, and also to the use of gelatinising agents, such as xanthan, in these methods.

12 Claims, 3 Drawing Sheets

METHOD FOR INCREASING THE GROWTH RATE OF CELLS IN STATIC LIQUID MEDIA

BACKGROUND OF THE INVENTION

1. Field of the Invention

The present invention relates to a method for increasing the growth rate of cells, and increasing the expression of genes in these cells, in static liquid media by using gelatinising agents in the medium, and to the use of gelatinising agents, such as xanthan, in such methods.

2. Description of the Related Art

The full citation to the references cited herein may be found in the References section below.

Suitable growth conditions for using artificial nutrient media were described a long time ago for a number of microorganisms such as bacteria or fungi, for example S. cerevisiae, B. cinerea, S. tritici, M. grisea, P. infestans or R. solani. Such artificial media are also known for mammalian cell or insect cell cultures and for plant cell cultures. These media are also used, for example, in high-throughput methods based on using cell cultures. Thus, S. cerevisiae, for example, has been successfully used in cell-based assays in HTS-experiments. However, it is likewise known that, while growth or germination on plate media is possible for a large number of different cell types, such as fungi, culture in liquid media is either not possible or very elaborate and consequently unsatisfactory (e.g. rust fungi, oomycetes). A third group of fungi, i.e. what are termed obligatory biotrophic fungi, cannot be maintained on artificial media. These are fungi which enter into a long-term nutritional relationship with the living cells of their host. In principle, the culture of cells in liquid media requires that the media be thoroughly mixed continuously, i.e. shaken, in order to ensure that the cells are supplied with nutrients. For this reason, most cells, e.g. fungal cells, are poorly suited, or not suited, for HTS methods in which the liquid media cannot be shaken and are consequently static. However, as a rule, HTS methods require the growth, or at least the survival, of the cells. In addition to this, it is as a rule necessary for a reporter gene to be expressed. The use of a high cell density is no way out in this context since a cell density which is too high renders measurements of the optical density or the fluorescence impossible. These problems will be further clarified with the aid of the following example.

In addition to the yeast fungi which have been mentioned, there are other fungi which possess outstanding growth properties both in solid media and in liquid media. A representative of this group is the phytopathogenic basidiomycete Ustilago maydis. U. maydis is described as being a dimorphic fungus. In the haploid stage, it exhibits yeast-like growth (sporidium), with a generation time of about two hours in complete medium. By contrast, the second growth form, the dikaryotic filament, does not proliferate on artificial media. For this reason, the haploid sporidia are the main form in which U. maydis is cultured. In order to achieve optimum growth, it is necessary to grow the cultures while shaking.

If, on the other hand, a U. maydis culture is transferred to a static solution, which is not constantly shaken or thoroughly mixed, such as in a 384-well MTP (MTP ≙ microtiter plate), it is then not possible to observe any increase in the optical density (FIG. 1); consequently, no growth takes place. It is therefore not possible to grow, and use, fungal cells such as U. maydis cells in such static fluid media. This is a problem, in particular, when only an in vivo test is possible, or desired, in a particular experimental arrangement due to the specific properties of a target, of a specific enzyme test or of the measurement method employed. These targets include, inter alia, targets such as membrane proteins or receptors, and also polypeptides whose purification from a cell is difficult or associated with a loss of the activity of the polypeptide.

Figure 2:
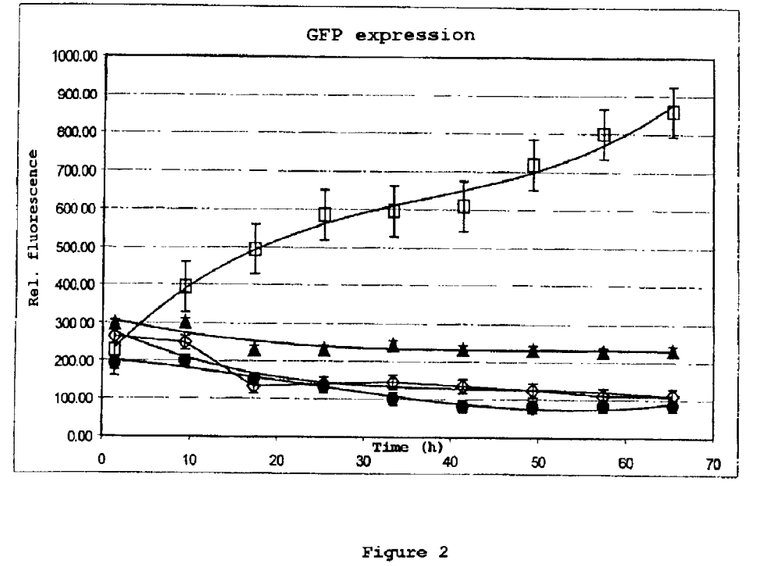
FIG. 2 illustrates reporter strain-specific and Kelzane®-dependent increase in the GFP fluorescence in 384-well MTPs. The figure shows the time-dependent change in the relative fluorescence due to expression of the reporter gene product GFP in 384-well MTPs. The curves marked out by boxes and filled triangles show the relative fluorescence in strain UMA3 with and without Kelzan®, respectively. The curves marked out by rhombi and filled circles, respectively, depict the relative fluorescence in strain Um521 with and without Kelzan®. The standard error of the measurement series is also indicated in each case.
Figure 3:
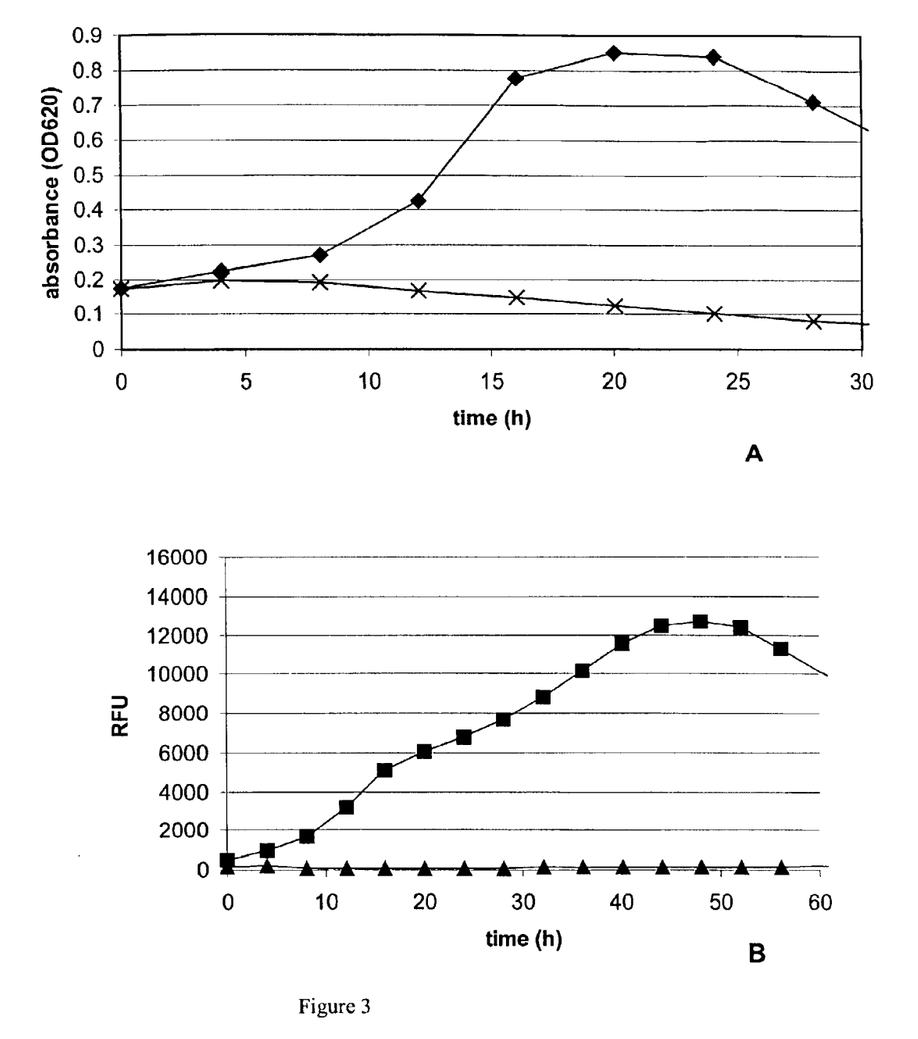
FIG. 3 illustrates growth-assay of *U. maydis* strains in 384 well MTPs.

Furthermore, in cells which harbour a constitutively expressed reporter gene, it is either not possible to observe any increase in the expression or only possible to observe a trivial increase in the expression (FIG. 2). This has to date made it impossible to use the abovementioned fungal cells in static liquid media.

The above mentioned problems consequently have a negative effect in the high-throughput search for novel, in the case of the above mentioned example fungicidal, active compounds which belong to new active compound classes and/or have new sites of action. Sites of action, that is targets or polypeptides, or else DNAs or RNAs, which cannot, in the customary manner, be overproduced in a bacterial host, purified and used in in-vitro HTS assays are therefore only accessible with great difficulty. Consequently, screening for a number of interesting targets cannot be performed on account of technical problems. However, it is frequently precisely the use of the organisms, e.g. fungi, in which it has been possible to identify these targets which is suitable for expressing the polypeptide in question and testing it directly in vivo. However, the above-described problems have thus far prevented particular cells or organisms, such as the above mentioned fungi, from being used for this purpose.

SUMMARY OF THE INVENTION

The object of the present invention was therefore to make available a method which can be used to ensure or increase the growth of cells, and the expression of polypeptides, in static liquid media.

Within the context of the present invention, it has now been found that the deficient growth of the cells is to be attributed to the fact that they sink down to the bottom of the receptacles, e.g. of the microtiter plates, resulting in the necessary supply of oxygen and nutrients no longer being maintained. The oxygen saturation of the medium in the well depends on the rate of diffusion and on the surface area of exchange with the air, which are only very low in the above-described static liquid media. Another problem can be what is termed contact inhibition of cell growth, with cells ceasing to proliferate as soon as they come into contact with each other (e.g. osteoblasts).

Problems which are analogous to those described above arise in the case of all cells which sink down in liquid cultures and can only grow in a significant quantity when the medium is thoroughly mixed constantly, for example in a shaker, thereby ensuring that the cells are supplied with nutrients and oxygen. This can affect plant cells, mammalian cells or insect cells. Even S. cerevisiae cells, which are also able to grow under anaerobic conditions, exhibit a markedly improved propagation rate when oxygen is supplied. The term "cells", as used herein, therefore encompasses all the cell types and cell culture types which are mentioned here, that is, for example, fungal cells, plant cells, mammalian cells and insect cells.

The object of the present invention was to make available a method which ensured the growth of cells in motionless liquid media, which method constantly makes it possible to use the cells in the said static media.

BRIEF DESCRIPTION OF THE DRAWINGS

FIG. 1 illustrates Kelzan®-dependent growth of U. maydis cells in 384-well MTPs. The growth is shown as an increase in the optical density, at a wavelength of 620 nm, in dependence on time. The curve marked out by filled circles depicts the average increase in the $OD_{620}$ in the presence of Kelzan®, while the curve marked out by open triangles depicts the change in $OD_{620}$ without Kelzan®. The curves which depict the changes in the $OD_{620}$ in the medium control without cells with and without Kelzan®, respectively, are depicted by open rectangles and open rhombi, respectively. The black bars indicate the standard error of the measurement in each case.

A: The kinetik of the absorbance at OD620 for *U. maydis* wildtype strains was determined in a 384 well MTP using a Tecan ultra reader (rombus). As control served a strain, to which Hygromycin B was added in a concentration of 200 µg/ml (crosses). The initial OD620 for both strains was 0,18. The strain without Hygromycin showed an increase in OD until 20 h after start, while in the presence of Hygromycin B the same strain showed a continuous decrease in optical density.

B: Kinetik of GFP expression in a transgenic *U. maydis* strain in 384 well MTPs. GFP fluorescence of a *U. maydis* strain, in which GFP expression is controlled by the strong constitutive OMA promoter (squares), was determined in a Tecan plus reader. The excitation wavelength was 485 nm, the emission wavelength was 535 nm. As control served an *U. maydis* wildtype strain, that does not express GFP (triangel). Over the time the transgenic strain showed an increase in GFP-fluorescence with a maximum after 50 h, while the wildtype strain does not show fluorescence. Compared to lower temperatures, the increase in OD620 and the increase in fluorescence was faster. Experimental procedures: *U. maydis* strains where treated as described before in the Examples. The solution contained 1×minimal medium, 0,1% Kelzan and the assay was performed at 30° C. All experiments where repeated in independent duplicates.

DETAILED DESCRIPTION OF THE INVENTION

Adding a Gelatinising Agent Enables *U. maydis* to Grow in 384-well MTPs

It has now been found, surprisingly, that adding suitable concentrations of a gelatinising agent to the liquid medium enables cells such as fungal cells to grow, a finding which can be demonstrated on the basis of the increase in optical density and the elevated expression of a reporter gene.

In this connection, the term "gelatinising agent", as used herein, encompasses all substances, compounds or substance mixtures which, in liquids, result in the formation of a gel or the formation or increase of a structure or texture and/or viscosity. In an alternative definition, substances which are suitable for maintaining cells in suspension in a medium are termed "gelatinising agents".

With the aid of the present invention, the supply of oxygen and nutrients, for example, to the cells is now improved by adding a gelatinising agent, which maintains the cells in suspension, to the liquid medium.

In this connection, the present invention is not restricted to specific media provided the medium concerned is suitable for the cell culture employed and for the purpose for which the cell culture is to be used. That is, the medium must, for example, be suitable for the measurement method, for determining the growth of the cells or the activity of a particular gene product, which is to be used in connection with the selected cell culture or the selected reporter gene. Thus, when green fluorescent protein (GFP) is used as the reporter gene in a cell culture, care must be taken to ensure that the medium does not have any fluorescence of its own. Thus, what is termed the potato dextrose medium (Tsukada et al., 1988), for example, would not be suitable for fluorescence measurements based on eGFP since this medium interferes with the measurement in the wavelength range of eGFP. Measuring the growth of the cells, as a rule measuring the optical density, also demands a medium which does not have any influence on the OD measurement (media which contain blood are not, for example, particularly suitable in this context).

An example of such a gelatinising agent is what is termed Kelzan®, a xanthan polysaccharide (xanthan gum). As a result of the xanthan being present, the cells, e.g. fungal cells, remain uniformly distributed in the well and are in this way supplied with sufficient oxygen and nutrients and are not affected by contact inhibition. However, it is likewise also possible to use other gelatinising agents, which are described in more detail below.

In the case of *U. maydis* cells, for example, the optimum doubling time in a shaken flask is only 2.5 h. In the case of the *U. maydis* strain Um518, which was used by way of example, it was not possible to observe any doubling in static liquid medium lacking xanthan within the space of 65 hours. In the period investigated, the optical density only increased by about 75%. However, in medium containing xanthan, the cell number had already doubled after about 21 hours. The optical density of *U. maydis* triples within 65 hours if xanthan is added to the medium. As a result, the growth and proliferation conditions for the fungal cells are markedly improved, thereby making it possible to use the cells in methods which otherwise only allow the use of static cultures.

The Influence of Gelatinising Agents on the Expression of a Gene Product, as Exemplified by the Expression of GFP in *U. maydis* Reporter Strains in 384-well MTPs The growth test already shows the positive influence of gelatinising agents, such as xanthan, on the growth rate of *U. maydis* cells. Apart from the growth, the expression of polypeptides has hitherto been prevented at the same time, as previously described, thereby making it impossible to use fungal cells, for example, in in vivo test systems, for example in HTS assays. Frequently, the polypeptide of interest, which is to be tested, has first of all to be produced in an increased quantity (overproduced) in order to render possible activity tests which give an adequate signal. However, in the case of in vivo methods, it is also frequently necessary to use a reporter to monitor the activity, or the loss of activity, of a polypeptide or of a polypeptide complex. A typical example of a reporter is the green fluorescent protein (GFP), whose expression can be measured on the basis of its characteristic fluorescent properties.

Within the context of the present invention, an investigation was carried out, therefore, to determine whether the augmented growth, as described above, also has an effect on the expression of gene products, and/or whether the augmented growth is sufficient for ensuring adequate expression for activity tests or HTS. The intention was to investigate this, by way of example, on the basis of the expression of a reporter gene. In the case of *U. maydis*, the abovementioned GFP is particularly suitable for this purpose because it does not require any further exogenous or endogenous factors for its activity.

For determining the GFP fluorescence, use is made of the *U. maydis* strain UMA3, which expresses eGFP (Clontech: "enhanced green fluorescent protein") under the control of the constitutive otef promoter (see Example 3). In order to determine the background fluorescence, the GFP fluorescence was compared with the fluorescence in the wild-type strain Um518. The fluorescence in the strains was in each case determined with and without xanthan in the medium (minimal medium). As a further control, the medium employed was included in the investigation on its own (without cells), in each case with and without xanthan. The GFP-based fluorescence was determined in at least 36 wells at an excitation wavelength of 485 nm (10 nm band width) and an emission wavelength of 510 nm (10 nm band width) (Example 4, FIG. 2).

In this connection, it was possible to observe that, in the case of strain UMA3, there was a marked increase in the fluorescence in those wells which contained xanthan as the gelatinising agent in the medium. By contrast, it was not possible to observe any increase in GFP fluorescence in UMA3 strains which were incubated without any xanthan in the medium. A slight decrease in the fluorescence was even observed. The same applies to strain Um518, which does not harbour any GFP reporter gene. The reduction in GFP fluorescence is accordingly not dependent on the GFP reporter gene but has to be due to other causes. The medium controls did not exhibit any significant changes in fluorescence either (not shown).

It was consequently furthermore possible to demonstrate, within the context of the present invention, that the addition of gelatinising agents, such as xanthan, to media leads to a significant increase in protein expression in the cells. This presumably reflects the above-demonstrated improvement in growth rate which is achieved by adding these gelatinising agents. Gelatinising agents consequently create conditions in cultures of cells such as fungal cells, such as *U. maydis*, which bring about a significant increase in the rate of cell division. This is accompanied by a level of protein expression which is likewise significantly higher.

Consequently, the present invention makes it possible to carry out cell-based in vivo tests in methods such as HTS or UHTS, which tests were previously only to a limited extent accessible to these methods.

The present invention consequently relates to a method for increasing the growth rate of cells, preferably fungal cells, in static liquid media, characterized in that the medium contains a gelatinising agent, with xanthans or polyacrylamides being particularly preferred. The method according to the invention is particularly preferably suitable for use in cell cultures of *U. maydis*.

The present invention likewise relates to a method for increasing the expression of a gene in cell cultures, preferably fungal cell cultures, in static liquid media, characterized in that the medium contains a gelatinising agent, with xanthans or polyacrylamides being particularly preferred. The method according to the invention is particularly preferably suitable for use in cell cultures of *U. maydis*.

The present invention likewise relates to the use of gelatinising agents in static liquid media for increasing the growth rate of cell cultures, preferably fungal cell cultures, and for increasing the expression of a gene in cells, preferably fungal cells, with xanthans and polyacrylamides being particularly preferred. Particular preference is given, according to the invention, to being able to use xanthan in cell cultures of *U. maydis*.

The present invention likewise relates to the use of gelatinising agents in static liquid media in in vivo HTS or UHTS assays using fungal cell cultures, with xanthans being particularly preferred. Particular preference is given, according to the invention, to being able to use xanthan in HTS or UHTS assays using cell cultures of *U. maydis*.

Improving the Growth Rate of Cell Cultures

As explained above, methods have already been developed for certain fungi or fungal cells, for example, which methods allow these fungi/fungal cells to be used in HTS assays or in static liquid media. In the described methods, a range of fungal cells do not have any growth problems, resulting in preference having been given, and being given, to using these cells.

Fungi in which the abovementioned problems arise are, for example, those fungi which tend to sediment and/or aggregate in static liquid media and therefore, on the one hand, are no longer available for the customary methods of measurement and, on the other hand, no longer grow, or die off, as a result of the deficient supply of oxygen and nutrients. An example of these fungi is the basidiomycete *Ustilago maydis*, which is a plant pathogen. This fungus has by now been under investigation for a considerable time and is therefore also of special significance within the context of the important target research, that is the search for points of attack for novel fungicides. However, because of these growth properties of *U. maydis*, it has only been possible to a limited extent, and with substantial effort, to use what are termed targets which have been able to be identified and investigated in this organism and will continue to be found in the future, but which, due to problems in purification or their specific activity (membrane proteins, receptors, etc.), have thus far not been accessible for in vitro assays, for searching for novel active compounds. Rather, research workers are obliged to identify and/or express, and, where appropriate, purify the homologous genes in other, more suitable organisms.

However, these problems are not restricted to *U. maydis*. Other cells and other fungi can therefore, in an analogous manner, be made available for use in static liquid media, and consequently in HTS or UHTS assays, by employing gelatinising agents, such as xanthans, which are the gelatinising agents which are preferably used in this context. These other cells and fungi also include the fungus *S. cerevisiae*; while it has already been possible to use this fungus in static liquid media, because of its ability to live anaerobically, the method according to the invention can further improve its growth and its ability to express polypeptides.

Gelatinising Agents

There are a number of compounds, frequently biopolymers, but also synthetic polymers or mixtures thereof, which are able to form gels or aqueous gels and which can be used as stabilizers, emulsifying agents or thickeners or for forming hydrocolloids or texturing various media. These "gelatinising agents", as they are to be designated in this present case, in accordance with the above definition of this term, are used in foodstuff processing and also for industrial purposes, for example when drilling for oil. It is also known to use them for formulations, for example in seed treatment, where various polymers form an aqueous gel which promotes the germination of bioherbicides, such as the fungus *Alternaria cassiae* (Shabana et al., 1997).

An example of a synthetic polymer which is particularly well suited for use in the methods according to the invention is polyacrylamide. Polyacrylamide is formed by polymerizing acrylamide monomers. A gel is formed by crosslinking with bifunctional compounds such as N,N'-methylenebisacrylamide. The pore size in these gels can vary greatly, depending on the gel composition, and, in the method according to the invention, can be adjusted to the given requirements. Ammonium persulphate, which is frequently used as a starter for the polymerization (in combination with N,N,N',N'-tetramethylenediamine (TEMED)), can also be replaced with riboflavin in order to avoid the persulphate, which frequently interferes. The necessary free radicals are formed by photolysis of the riboflavin.

Naturally occurring polysaccharide compounds, whose use is customary practice in foodstuffs, in particular, are of particular interest. On account of their specific properties, which are explained in more detail below using the example of xanthans and/or kelzan, these polymers are well suited for the above-described method according to the invention. The substances which are described in more detail below are examples of these polysaccharide gelatinising agents.

Arabinogalactan occurs naturally, at a content of from 5 to 35%, in the heartwood of larch species. The polysaccharide consists of a chain of β-D-galactopyranosyl residues which are linked by way of (1,3) bonds. At individual building blocks, the main chain carries side chains composed of galactose and arabinose residues. The degree of branching is high. The molecular weight is between 50 and 70 000 daltons. Because of its spherical structure in aqueous solution, a solution behaves as a Newtonian liquid. The viscosity is very low. There is virtually no dependence on the pH. Only at concentrations greater than 60% does the consistency of the solution change into that of a thick paste. Owing to its very good solubility, arabinogalactan is used, at low viscosity, as an emulsifier, a stabilizer and as a carrier material in ethereal oils, flavour formulations and sweeteners.

Amylose, see starch.

Agar is obtained by hot water extraction from a variety of red algae (Rhodophyceae: *Gelidium* spp., *Pterocladia* spp. and *Gracilaria* spp.). In addition to producing agar and carrageen, these algae also produce galactans. Agar is not a precisely defined material. It consists of β-D-galactopyranose and 3,6-anhydro-α-L-galactopyranose which are alternately linked by way of 1,4 bonds and 1,3 bonds. Some of the chains are esterified with sulphuric acid. Agar is differentiated, according to the sulphate content, into agarose (approx. every $10^{th}$ galactose residue is esterified) and agaropectin (higher degree of esterification and use of pyruvic acid). Agar is insoluble in cold water. It is soluble colloidally on being boiled. When agar is cooled, a typical gel formation can be observed at about 45° C. In this connection, it is noteworthy that the gelling temperature and the melting temperature diverge when the agar is heated once again. For example, a 1.5% solution gels at a temperature of from 32 to 39° C. and only melts once again at from 60 to 97° C. The properties and stability of the gel which has been formed depend on the concentration and on the molecular weight. Agar is already used for solid nutrient media in microbiology and as a thickener in the foodstuffs industry.

Amylopectin, see starch.

Alginates are found in the cell walls of all brown algae. Alginate is obtained by being extracted from the brown algae (Phaeophyceae: *Macrocystis pyrifera*, *Laminaria* spp., *Ascophyllum* spp, and *Sargassum* spp.) using alkali. The polysaccharide is then precipitated from the resulting extract as calcium salt (E404) or as alginic acid (E400). Alginate consists of β-D-mannuronic acid and α-L-guluronic acid, which are linked by way of 1,4 bonds. The molecular weight is in the region of from 32 000 to 200 000 daltons, corresponding to a degree of polymerization of 180 units. The salts which are formed with alkali metals, magnesium, ammonia and amines are water-soluble and are used as thickeners. The viscosity of alignate solutions depends, in particular, on the molecular weight and the given counterion. Particularly in the presence of polyvalent cations (e.g. calcium), it increases with the concentration of these ions and can therefore easily be adjusted to the desired values. Gels, fibres and films can be prepared by selectively adding calcium ions or by acidifying sodium alginate solutions. Alginates are very effective thickeners, stabilizers and gelatinising agents. In concentrations of from 0.25 to 0.5%, they improve, for example, the stability of fillings for cakes and pastries and stabilize salad dressings, chocolate milk and ice-cream.

Carrageen is a sulphate-containing galactan, such as κ-carrageenan, which can be extracted from red algae. Carrageenan consists of D-galactose-4-sulphate and 3,6-anhydro-α-D-galactose which are alternately glycosidically linked in the 1,3 and 1,4 position, is readily soluble in water and, on being cooled, forms thixotropic gels, with liquefaction beginning in the presence of $Na^+$ ions and at relatively low pH values.

Cellulose is the main constituent in plant cell walls. It is found together with hemicelluloses, pectin and lignin. Cellulose consists of β-glucopyranose residues which are linked by way of 1,4 bonds. Crystalline structures are formed due to the chain structure. In native cellulose, the proportion of crystalline segments is about 60%. The cellulose chains are also somewhat folded, such that intramolecular hydrogen bonds can be formed, which bonds additionally increase the ordered structure (H bonds between O(4) and O(6) and also between O(3) and O(5)). Cellulose has a high molecular weight. Depending on origin, degrees of polymerization of from 1 000 to 14 000 are quoted. Because of its highly ordered structure and its high molecular weight, cellulose is not soluble in water. While the ability of cellulose to swell varies depending on the origin of the cellulose, this ability is basically low. The poor hydratability and dispersibility are markedly improved by adding small quantities of carboxymethylcellulose. Cellulose, which is stable, can be converted by alkylation into a number of derivatives which are then readily swellable and soluble, depending on the modification. These compounds are referred to as cellulose derivatives, which, because of their many and varied properties, have many applications.

Curdlan, the generic name for a beta-(1,3)-D-glucan, is the most concentrated form of a beta-glucan, the original route for preparing which comprised fermenting a glucose medium with *Agrobacterium biovar* 1. Curdlan is a hydrocolloid former and a good texture former whose gels are stable over a wide pH range.

Dextran is produced, using sucrose as substrate, by *Leuconostoc mesenteroides* and *L. dextranicum*. Dextran is a β-1,6-glucan possessing some glucose side chains which are principally linked to the main chain by way of 1,3, but in some cases also 1,4 and 1,2, bonds. Dextran is readily soluble in water.

Furcellaran is obtained from the red alga *Furcellaria fastigiata*. Furcellaran consists of D-galactose (from 46 to 53%), 3,6-anhydro-D-galactose (33%) and of sulphates of both sugars (16 to 20%). The structure is very similar to that of κ-carrageen. The essential difference is that κ-carrageen contains one sulphate residue for every two sugar residues, whereas in Furcellaran there is one sulphate residue for every three to four sugar residues. Furcellaran forms thermoreversible gels. The ability to gel depends on the degree of polymerization, on the content of 3,6-anhydro-D-galactose and on the cations which are present in solution. While potassium forms solid gels, calcium has little effect. Sodium does not give rise to any gel formation. Sugar has a positive influence on gel formation.

While glycogen resembles amylopectin in its structure, it exhibits an even greater degree of branching and a higher molecular weight (from 25 000 to 90 000 D-glucose units).

Guar, which is obtained from the seeds of *Cyamopsis tetragonolba* (Leguminosae) by separating off the outer layers and the embryo, contains, in addition to the polysaccharide guaran, from 10 to 15% water, from 5 to 6% protein, 2.5% crude fibre and from 0.5 to 0.8% ash, and consists of β-D-mannopyranosyl residues which are linked by way of 1,4 bonds, with every second residue possessing by way of a 1,6 bond, α-D-galactopyranosyl residues as a side chain. Guaran forms highly viscous solutions whose viscosity depends on the shearing stress.

Gum arabic, which is obtained as a resin from the sap of various acacia species (*Acacia* spp.) and mimosa species, is a mixture of closely related polysaccharides having an average molecular weight which can vary, depending on origin, in the range from 260 000 to 1 160 000 daltons. The sugar residues L-arabinose, L-rhamnose, D-galactose and D-glucuronic acid serve as the building blocks, with the main chain consisting of 1,3-linked β-D-galactopyranosyl residues whereas the side chains are 1,6-linked. Gum arabic is extremely water-soluble, such that it is possible to prepare concentrations of up to 50%. In contrast to other polysaccharides, the viscosity only increases at high concentrations.

Carob bean flour is obtained from the siliquae (pods) of the carob tree (*Ceratonia siliqua*). In order to obtain the carob bean flour, the seeds are ground and the endosperm is separated off. The flour then contains about 88% galactomannoglycans, 5% of other polysaccharides, 6% protein and 1% mineral substances. As in the case of the guaran (see "guar"), the polysaccharide of carob bean flour consists of a chain of β-D-mannopyranosyl residues which are linked by way of 1,4 bonds. In contrast to guaran, α-D-galactopyranosyl residues are only present as side chains (1,6 bonds) on every $4^{th}$ to $5^{th}$ mannose residue. The molecular weight is about 310 000 daltons. The properties correspond to those of guaran. At the same concentration, the viscosity of the solutions is somewhat lower. Carob bean flour has a favourable structural viscosity.

Pectin is obtained from citrus fruit peel and from apple residues. The extracts are either concentrated, to give rise to liquid pectin preparations, or processed into powders by means of spray drying and drum drying. In its main structure, pectin consists predominantly of 1,4-linked α-D-galacturonic acid (Homogalacturonan) and branched regions whose backbone is alternately composed of 1,4-linked α-D-galacturonic acid and 1,2-linked α-L-rhamnose (Rhamnogalacturonan). The main building blocks of the side chains are arabinose and galactose, which are linked. Relatively small quantities of monosaccharides, such as apiose, L-aceric acid, 2-keto-3-deoxyoctonic acid, 3-deoxy-D-xylo-2-heptulonic acid and two different methylated monosaccharides are also found in pectin. The building blocks of pectin can be esterified with methanol or acetic acid at various sites. Pectin achieves its greatest chemical stability at a pH of from 3 to 4. Pectin is a readily swellable carbohydrate. In addition to this, it also forms thermoreversible gels in the range around pH 3 and in the presence of calcium ions. The ability to form gels is proportional to the molecular weight and inversely proportional to the degree of esterification, provided the same conditions otherwise pertain.

Starch is an important storage polysaccharide in plants and can be subdivided into two fractions: amylose is an unbranched starch consisting of glucose molecules which are linked linearly by way of α-1,4 bonds. In corn starches, the degree of polymerization is between 1000 and 2000. These chains must in turn, depending on the solution state, be imagined as being more or less pronounced helices. It is difficult to disperse amylose in cold water. On heating, swelling occurs and a starch paste is formed. This paste is a system of swollen starch grains in a starch solution. In this connection, reference is made to the glutinization temperature. This temperature differs depending on the starch. When a starch paste is cooled rapidly, a different texture is formed depending on whether the mixture is stirred or not. When the mixture is stirred, the viscosity generally increases, whereas an amylose gel is formed when the mixture is not stirred. Amylopectin is a branched starch containing α-1,4 and α-1,6 bonds between the glucose molecules. In this connection, the branches in the chain are effected by way of α-1,6 bonds. These branches are irregularly present at about every 15–30 glucose segments. The molecular weight of amylopectin is very high, being in the range from $10^7$ up to $2 \times 10^8$ daltons. It is assumed that amylopectin also forms helices within certain limits. Amylopectin is soluble in hot water. It gives rise to clear, highly viscous solutions which are stringy or cohesive. In contrast to amylose, amylopectin has scarcely any tendency to undergo retrogradation. Except at very high concentrations, it is not possible to observe any ageing and gel formation. Natural starch is a mixture of these two starch fractions, with the proportion depending on origin. Most starches contain from about 30 to 40% amylose and consequently mainly consist of amylopectin.

Scleroglucan, which is obtained from sclerotium species (*Sclerotium glucanicum*) which require a nutrient medium consisting of glucose, nitrate and mineral salts, is a polysaccharide which is precipitated with alcohol following filtration. Scleroglucan is a β-1,3-glucan which possesses a glucose residue, as a side chain, on about every third sugar and has a molecular weight of about 130 000 daltons. Scleroglucan is readily soluble in water and gives rise to high viscosities, with these solutions exhibiting a pseudoplastic behaviour.

Tragacanth, which is obtained from exudates of the plant *Astragalus* spp., is a plant gum which consists of two fractions: tragacanthin is soluble in water; by contrast, bassorin is insoluble, with the soluble fraction being a mixture of various polysaccharides (consisting of D-galacturonic acid, D-galactose, L-fucose, D-xylose and L-arabinose). The tragacanthin molecule has a molecular weight of approx. 840 000 daltons and is extended, resulting in highly viscous solutions whose viscosity depends on the shearing speed which is applied.

Xanthan is formed, for example, by *Xanthomonas campestris* and some related microorganism species. The polysaccharide is isolated from the medium by precipitating it with isopropanol in the presence of KCl. Xanthan is a heteroglycan which contains D-glucose, D-mannose, D-glucuronic acid, acetate and pyruvate in the molar ratio 28:30:20:17:5.1–6.3. The molecular weight varies from $2 \times 10^6$ to $12 \times 10^6$, depending on the preparation conditions and the strain employed. Xanthan is readily soluble in cold and hot water, with the helices which form giving rise to a three-dimensional network which results in high viscosities. Xanthan therefore exhibits pseudoplastic behaviour in highly viscous solutions. In this connection, the viscosity is to a large extent independent of the temperature. In the presence of xanthan, solutions, emulsions and gels possess high freeze-thaw stability. Xanthan is used for pressure stabilization and for stabilizing emulsions of ethereal oils in drinks. Because of its high degree of thermal stability, it is also used as a thickener in tinned foods. Adding xanthan improves freeze-thaw stability in starch gels. A high degree of stability is achieved in the resting state whereas the fall in viscosity in connection with a shearing stress brings about a slight flux. Xanthans are particularly well suited for use in the methods according to the invention.

An example of a xanthan is the abovementioned Kelzan® (CAS#: 11138-66-2). Kelzan® is active up to a temperature of 130° C. The polymer is slightly anionic, for which reason the process of mixing with a solution which is cationic must be carried out with care. Kelzan® is very particularly suitable for use in the above-described methods according to the invention.

The concentration of the gelatinising agents and/or their degree of crosslinking can be varied and adjusted, in simple experiments, to the medium which is present, to the cells which are used and to the intended purpose as long as care is taken to ensure that, on the one hand, the cells do not sink down, or only do so sufficiently slowly, and, on the other hand, the solution can still be pipetted and any measurements which are made are not interfered with. It is also important that the concentration be adjusted such that the air bubbles which may possibly be formed when the medium is mixed with cells are able to rise upwards and escape, since these air bubbles would otherwise crucially interfere with measurements.

In the case of the xanthans (e.g. Kelzan®) the concentration can be varied over a relatively wide range. A concentration of from 0.06 to 0.3% by weight has been found to be particularly suitable, with a concentration of from 0.08 to 0.2% by weight being particularly preferred. Optimal results were obtained at a concentration between 0.09 and 0.12% by weight, in particular 0.1% by weight.

As a rule, the temperature range in which the gelatinising agents can be used is large and can be deduced from the abovementioned comments or from the specialist literature. The temperature ranges of from 18 to 38° C., which are of interest for cell cultures, constitute a problem for hardly any gelatinising agents.

In the case of the xanthans, in particular Kelzan®, very good results were obtained at a temperature of from 16 to 37° C., particularly at a temperature of from 22 to 34° C., with good results being obtained, in particular, at 28° C. to 30° C. Optimal results were obtained at 30° C.

As a rule, the gel-forming effect of the gelatinising agents is independent of the volume introduced. For example, xanthans (e.g. Kelzan®) were successfully employed, according to the invention, in cell cultures in 384-well MTPs (100 μl) and in cell cultures in Erlenmeier flasks (800 ml).

In addition to Kelzan®, there are a number of other xanthans which possess similar properties and can therefore be used, in the same way, in the method according to the invention. The special properties are also to be found in the abovementioned gelatinising agents, such as starch or cellulose, which, as a result of the ability to form network-like structures, and consequently a viscous solution, are suitable, to the same extent as the abovementioned xanthan or Kelzan®, for use in the method according to the invention. However, the above list is not exhaustive. Rather, the intention is to use the given list to draw the attention of the reader to the fact that the gelatinising agents which can be used in accordance with the invention can be characterized, within the meaning of this invention, inter alia, by the ability to develop viscosity in a solution and, where appropriate, by pseudoplastic and stabilizing properties.

The varying properties with regard to temperature tolerance, preferred pH, ion dependence, development of viscosity or of networks, etc. can be used for finding the appropriate gelatinising agent for each given case in dependence on the medium employed, the cells which are used, and their requirements, and the measurement method employed for observing the expression and activity of a polypeptide. For this, the abovementioned properties can be taken into consideration, or the suitability of a gelatinising agent, and the optimum conditions, can be tested, in an obvious manner, in series of experiments.

In this connection, the fundamental demands placed on the gelatinising agents for their use in a method according to the invention are:

a) the ability to maintain cells in suspension in a medium, with it being necessary to determine the concentration of the gelatinising agent which is suitable in each case, b) the gelatinising agents must be optically and chemically inert, with, however, it being possible, where appropriate, for the gelatinising agents also to serve as a nutrient source, c) the gelatinising agents must not exert any osmotic pressure on the cells, and d) the gelatinising agents must, where appropriate, still enable the medium (where appropriate, together with the cells) to be pipetted.

EXAMPLES

Example 1

Conditions for Growing *U. maydis*

*U. maydis* cells were cultured, at 28° C., in PD medium up to an $OD_{600}$ of from 0.6 to 1.0. After that, they were centrifuged down at 3200 rpm for 10 min, washed with minimal medium and subsequently resuspended in minimal medium or minimal medium containing 0.1% Kelzan® such that the culture had an $OD_{600}$ of 0.3. The following calculation can be enlisted for achieving this:

$$V(x)=V(y)*OD_{600}(y)/OD_{600}(x)$$

V Volume
x: Fungal culture in PD medium from the overnight culture
y: Fungal culture in minimal medium, or minimal medium containing 0.1% Kelzan®, which is used in the MTP test.

Figure 1:
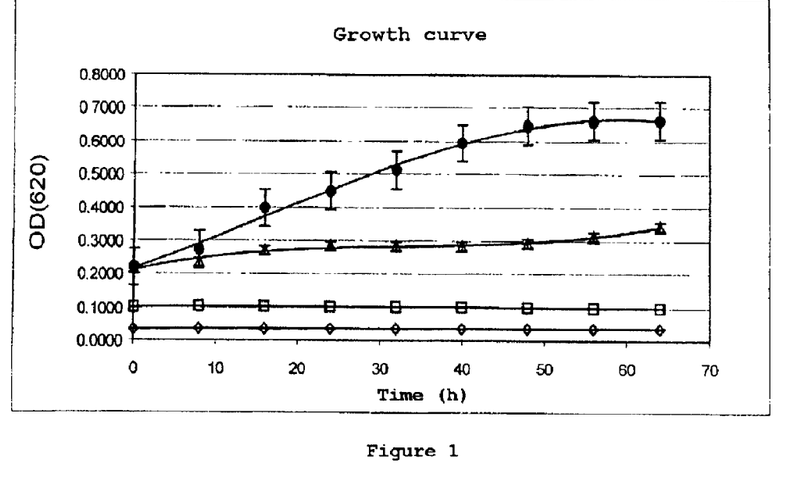

For the growth test, in each case 50 μl of cell suspension were pipetted into 384-well MTPs (transparent, from Greiner) using a Multidrop Pipetter. For the growth test, the absorption was determined at a wavelength of 620 nm. The plates were incubated at room temperature for three days. The optical density was determined in a Tecan plus reader at time zero and every four hours after that (FIG. 1).

*U. maydis* Strains Employed

The *Ustilago maydis* strains Um518 (a2b2) and UMA3 (a2b2 pCA123) were used for the experiments which were performed.

| Media employed | |
| --- | --- |
| PD medium | 2.4% (w/v) potato dextrose broth |
| Minimal medium (MM) | 0.3% (w/v) KNO$_3$ |
| | 6.25% (v/v) salt solution in accordance with Holliday, 1974 |
| | 1.0% (w/v) glucose |
| Salt solution | 160% (w/v) KH$_2$PO$_4$ |
| (in accordance with | 4.0% (w/v) Na$_2$SO$_4$ |
| Holliday, 1974) | 8.0% (w/v) KCl |
| | 4.08% (w/v) MgSO$_4$ * 7H$_2$O |
| | 1.32% (w/v) CaCl$_2$ * 2H$_2$O |
| | 8.0% (v/v) trace elements in accordance with Holliday, 1974 |
| Trace elements | 0.06% (w/v) H$_3$BO$_3$ |
| (in accordance with | 0.14% (w/v) MnCl * 4H$_2$O |
| Holliday, 1974) | 0.4% (w/v) ZnCl$_2$ |
| | 0.4% (w/v) Na$_2$MoO$_4$ * 2H$_2$O |
| | 0.1% (w/v) FeCl$_3$ * 6H$_2$O |
| | 0.04% (w/v) CuSO$_4$ * 5H$_2$O |

Example 2
Growth Test Using *U. maydis* Cells and Kelzan®

The influence of the presence of 0.1% Kelzane® in the medium on the growth rate of the *U. maydis* cells was investigated using a growth test (M&M). For this, *U. maydis* wild-type strain Um518 was incubated in MT plates in minimal medium with 0.1% Kelzan® and without Kelzan®. For the control, the optical density of the minimal medium on its own, and of the minimal medium containing 0.1% Kelzan®, respectively, was determined in parallel with this. The absorption was measured at a wavelength of 620 nm every 4 h in 36 independent wells. The measurements were carried out over three days (65 hours), with a measurement being made every 4 h.

Example 3
Construction of Plasmid pCA123 for Measuring the Expression of GFP in Liquid Medium The otef promoter was isolated, as an 890 bp PvuII/NcoI fragment, from the plasmid potef-SG (Spellig et al., 1996) and ligated into the vector pTEF-SG (Spellig et al., 1996), which had been cut with PvuII/NcoI. The SGFP gene was excised from the resulting plasmid by restricting with NcoI/NotI and replaced with the NcoI/NotI-cut EGFP allele from pEGFP-N1 (from Clontech). The resulting plasmid is termed pCA123.

Example 4
Determining the Expression of the Reporter Gene GFP

In each case, 50 μl of cell suspension from strains to be tested were transferred, as described above, into 384-well MTPs (black, from Greiner). The relative fluorescence due to the expressed GFP was determined fluorimetrically, in a Tecan plus reader, at an excitation wavelength of 485 nm (bandwidth 10 nm) and an emission wavelength of 510 nm (bandwidth 10 nm) and a gain factor of 70 at 3 flashes/measurement. The measurements were made at time zero and every 4 h after that (FIG. 2).

References

1. Holliday, R. (1974) *Ustilago maydis*. In King, R. C. (ed) Handbook of Genetics. Vol.1, Plenum, New York, pp. 575–595.
2. Shabana, Y. M., Charudattan, R., DeValerio, J. T., Elwakil, M. A. (1997): An evaluation of hydrophilic polymers for formulating the bioherbicide agents *Alternaria cassiac* and *A. eichhorniae*. Weed Technology 11, 212–220.
3. Spellig T, Bottin A, Kahmann R (1996): Green fluorescent protein (GFP) as a new vital marker in the phytopathogenic fungus *Ustilago maydis*. Mol. Gen. Genet. 252, 503–509.
4. Tsukada, T., Carleton, S., Fotherinham, S. and Holloman W. K. (1988): Isolation and characterization of an autonomously replicating sequence from *Ustilago maydis*. Mol. Cell. Biol. 8, 3703–3709.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method for increasing the growth rate of cells in a static liquid culture comprising:

(a) providing a liquid medium for growing one or more cells, which liquid medium contains a xanthan polysaccaride in an amount sufficient to suspend the cells in the liquid medium and to allow oxygen diffusion into the medium sufficient to promote cell growth while the liquid medium is static;

(b) providing cells in need of being grown;

(c) suspending the cells in the liquid medium; and (d) growing the cells in the liquid medium while maintaining the liquid medium static.

2. The method according to claim 1 wherein the liquid medium allows measurement of cell growth.

3. The method according to claim 2 wherein the measurement of the cell growth is by fluorescence or by optical density.

4. The method according to claim 1 wherein the temperature of the medium is maintained from 16 to 37° C.

5. A method for increasing the expression of a gene in cells in a static liquid culture comprising:

(a) providing a liquid medium for growing one or more, cells which liquid medium contains a xanthan polysaccaride in an amount sufficient to suspend the cells in the liquid medium and to allow oxygen diffusion into the medium sufficient to promote gene expression in the one or more cells while the liquid medium is static;

(b) providing cells in need of increased gene expression;

(c) suspending the cells in the liquid medium; and (d) culturing the cells in the liquid medium to promote gene expression while maintaining the liquid medium static.

6. The method according to claim 1 or 5 wherein the xanthan polysaccaride is present at a concentration of from 0.08 to 0.3% by weight.

7. The method according to claim 6 wherein the xanthan polysaccaride is present at a concentration of from 0.09 to 0.12% by weight.

8. The method according to claim 7 wherein the xanthan polysaccaride is present in a concentration of about 0.1%.

9. The method according to claim 1 or 5 wherein the cells are plant cells, mammalian cells, or insect cells.

10. The method according to claim 9 wherein the cells are fungal cells.

11. The method according to claim 10 wherein the fungal cells are *Ustilago maydis* cells.

12. The method according to claim 1 or 5 wherein after the period of rest, the cell culture is pipetted.

* * * * *